(12) United States Patent
Millet et al.

(10) Patent No.: US 10,959,469 B2
(45) Date of Patent: Mar. 30, 2021

(54) DEVICE FOR PROTECTING THE PLANTAR PADDING, IN PARTICULAR DURING A SPORTING ACTIVITY

(71) Applicant: MILLET INNOVATION, Loriol sur Drome (FR)

(72) Inventors: Damien Millet, Valence (FR); Odile Grange, Allex (FR); Thierry Fontaine, Marsanne (FR)

(73) Assignee: MILLET INNOVATION, Loriol sur Drome (FR)

( * ) Notice: Subject to any disclaimer, the term of this patent is extended or adjusted under 35 U.S.C. 154(b) by 273 days.

(21) Appl. No.: 15/539,756

(22) PCT Filed: Dec. 17, 2015

(86) PCT No.: PCT/FR2015/053565
§ 371 (c)(1),
(2) Date: Jun. 26, 2017

(87) PCT Pub. No.: WO2016/102824
PCT Pub. Date: Jun. 30, 2016

(65) Prior Publication Data
US 2017/0347723 A1 Dec. 7, 2017

(30) Foreign Application Priority Data
Dec. 24, 2014 (FR) ........................ 1463309

(51) Int. Cl.
*A41D 13/06* (2006.01)
*A61F 5/01* (2006.01)
(Continued)

(52) U.S. Cl.
CPC .......... *A41D 13/06* (2013.01); *A41D 13/015* (2013.01); *A61F 5/019* (2013.01); *A61F 5/0109* (2013.01);
(Continued)

(58) Field of Classification Search
CPC .. A41D 13/06; A41D 13/015; A41D 2400/82; A41D 2400/80; A61F 13/067;
(Continued)

(56) References Cited

U.S. PATENT DOCUMENTS 1,741,340 A * 12/1929 Scholl .................. A41B 11/006
2/239
3,299,894 A * 1/1967 Charlebois ............ A61F 13/068
36/140
(Continued)

FOREIGN PATENT DOCUMENTS

FR 2712487 A1 5/1995
JP 02300302 A * 12/1990
JP 06105859 A * 4/1994

OTHER PUBLICATIONS

Mar. 4, 2016 International Search Report issued in Intenational Patent Application No. PCT/FR2015/053565.

*Primary Examiner* — Katherine M Moran
*Assistant Examiner* — Grace Huang
(74) *Attorney, Agent, or Firm* — Oliff PLC (57) ABSTRACT

A device protecting the plantar padding of a foot that includes a cushion including a viscoelastic material that is configured to be held against the skin of the plantar region and to cover all of the metatarsal heads and the metatarsophalangeal joints of the foot, and an elastic band attached to the cushion along two opposing transverse edges and by a tab configured to pass between the big toe and the adjacent toe of the foot. The band has a width configured to entirely cover side bulges formed by the metatarsophalangeal joints of the small and big toes. A portion of the band configured for contacting the top of the foot includes tacky elements on both sides thereof, which prevent the protective device from (Continued)

sliding on the skin when the device is placed on the foot and inside a sock surrounding the foot.

13 Claims, 6 Drawing Sheets

(51) Int. Cl.
*A61F 13/06* (2006.01)
*A41D 13/015* (2006.01)

(52) U.S. Cl.
CPC ........ *A61F 13/067* (2013.01); *A41D 2400/82* (2013.01)

(58) Field of Classification Search
CPC .......... A61F 5/0109; A61F 5/019; A61F 5/12; A43B 7/26; A41B 11/004
USPC ........ 2/455; 602/30; 128/889, 892, 893, 894
See application file for complete search history.

(56) References Cited

U.S. PATENT DOCUMENTS

| | | | | |
|---|---|---|---|---|
| 4,084,265 A * | 4/1978 | Anfelt | ................ | A41D 19/0072 2/163 |
| 4,249,319 A * | 2/1981 | Yoshida | ................... | A43B 7/02 36/2.6 |
| 5,205,071 A * | 4/1993 | Hergenroeder | .......... | A43B 5/08 36/106 |
| 5,497,789 A * | 3/1996 | Zook | ..................... | A61F 13/063 128/893 |
| 5,607,749 A * | 3/1997 | Strumor | ................. | A43B 7/146 428/156 |
| 5,685,094 A * | 11/1997 | Lin | ...................... | A43B 1/0054 36/141 |
| 6,138,281 A * | 10/2000 | Chiaruttini | ............. | A41B 11/00 2/239 |
| 6,318,373 B1 | 11/2001 | Kasahara | | |
| 6,421,936 B1 * | 7/2002 | Gerrand | ................... | A43B 5/02 36/133 |
| 6,766,536 B1 * | 7/2004 | Aarons | ................ | A41B 11/008 2/161.3 |
| 7,056,299 B2 * | 6/2006 | Brown | .................. | A61F 5/0111 128/892 |
| 7,234,170 B2 * | 6/2007 | Simic | ................. | A41D 19/0058 2/16 |
| 7,383,591 B1 * | 6/2008 | Getzwiller | ............. | A63B 71/14 2/161.1 |
| 8,220,077 B1 * | 7/2012 | Ott | ........................ | A41B 11/008 2/239 |
| 9,585,434 B2 * | 3/2017 | Van Atta | ................ | A43B 5/025 |
| 9,609,896 B2 * | 4/2017 | Crosby | ................ | A41B 11/004 |
| 10,136,684 B2 * | 11/2018 | Meiselman | ........ | A41D 19/0006 |
| 2004/0221371 A1 * | 11/2004 | Kato | .................... | A43B 1/0054 2/239 |
| 2004/0261289 A1 * | 12/2004 | Lindsay | ................. | A43B 3/128 36/7.5 |
| 2005/0091729 A1 * | 5/2005 | Alley | .................... | A41B 11/004 2/239 |
| 2005/0144703 A1 * | 7/2005 | Hilbert | ................. | A41B 11/008 2/239 |
| 2006/0260024 A1 * | 11/2006 | Lee | ...................... | A41B 11/128 2/239 |
| 2007/0006486 A1 * | 1/2007 | Wilkenfeld | ............... | A43B 3/00 36/8.3 |
| 2008/0110045 A1 * | 5/2008 | Terlizzi | .................... | A43B 5/12 36/8.3 |
| 2009/0083993 A1 * | 4/2009 | Plank | ..................... | A43C 13/08 36/7.3 |
| 2010/0249686 A1 | 9/2010 | Rushton | | |
| 2010/0325922 A1 * | 12/2010 | Esposito | ................ | A43C 13/00 36/72 R |
| 2011/0183098 A1 * | 7/2011 | Hidalgo | ................. | C08C 19/22 428/36.9 |
| 2012/0011749 A1 * | 1/2012 | French | ..................... | A43B 13/22 36/59 R |
| 2013/0291272 A1 * | 11/2013 | Bourque | ............ | A41D 13/1161 2/9 |
| 2014/0250737 A1 * | 9/2014 | Bryne | ..................... | A43B 5/18 36/72 R |
| 2016/0095389 A1 * | 4/2016 | Minami | ............ | A43B 23/0245 36/45 |

\* cited by examiner

DEVICE FOR PROTECTING THE PLANTAR PADDING, IN PARTICULAR DURING A SPORTING ACTIVITY

BACKGROUND

Technical Field

The present invention relates to a device for protecting the foot, in particular for distributing loads applied to the front of the foot sole.

The foot has an absorbent shock layer called "plantar padding", capable of withstanding up to eight times the weight of the body. The plantar padding distributes the body's mechanical "load" to over the metatarsals. However, many patients suffer from heating, calluses or pain associated with unavoidable aging of the natural plantar padding, which then no longer functions as efficiently for distributing the load. As plantar padding ages, it tends to get thinner and harden. The foot may also be affected by skin conditions (irritations, cracking, plantar warts, etc.). In addition, practicing certain sports may be very demanding on the plantar padding and can lead to trauma, as well as a long-term degradation.

Related Art

In order to alleviate or prevent these pains and/or conditions, it is known to place under the metatarsal heads and/or under the metatarsophalangeal joints a cushion in a viscoelastic material chosen to distribute the load and avoid the formation of local hyperkeratosis, commonly referred to as callus. In order to make such a cushion, it is also known to use a polymer gel-based pad, such as silicone gel or hydrogel, to operate as a plantar padding substitute. Thus, such a pad, of a few square centimeters, may be made from a silicone gel composition based on PDMS (polydimethylsiloxane), for example marketed by the applicant under the name Epithelium 26®. French patent 2,712,487 describes such a silicone gel having properties approaching those of the plantar padding, which is used for the prevention of hyper-pressure zone pathologies appearing essentially on or under the feet.

The present invention is aimed more particularly at protecting the athletes' plantar padding. Athletes have a healthy plantar padding, but their sports practice leads to intense stress, which justifies a protection need to prevent immediate trauma and long-term degradation. However, the constraints related to the desired effect of such a pad on the skin often prove contradictory with the constraints of maintaining the pad on the area to be protected, or even with satisfactory practicing conditions of the sport concerned.

To ensure a load distribution function, it is known to use relatively hard silicone gel. However, silicone gels of this type are very weakly adhesive, and in any case insufficiently adhesive to hold naturally on the area to be protected. Moreover, in order to ensure a sufficient load distribution, the cushion must have a certain thickness, of several millimeters, which is also contradictory with the need of keeping the cushion on the area to be protected. Indeed, the thicker edges of the cushion are more likely to be snagged, causing the cushion to tear off. Stickier silicone gels exist, but they are softer, which makes them less resistant. They therefore have a reduced service life. It is indeed desirable for the cushion to have a long period of use and therefore withstand several washings. In any case, they do not lend themselves well to industrial production because they cannot be properly handled in an industrial process that includes the use of fabrics and stitching operations.

Since it is difficult to achieve adhesion of silicone gel to the skin naturally, it is known to maintain the cushion with elastic fabric retaining means. However, such retaining means may form inside the shoe a layer of material that adds to the sock layer, which may affect the comfort of the foot within the shoe. Moreover, the viscoelasticity of the cushion and it thickness should not reversely affect the posture of the user, statically or dynamically. For athletes, postural instability may have chain effects on muscles and joints, reversely affect the accuracy of their gestures and cause injury.

Moreover, during a sports activity, sudden direction changes and repetitive contact-point changes may cause a displacement of the cushion relative to the foot, in particular rotation about the foot.

The applicant has developed and sold a cushion adapted to elderly people having worn-out plantar paddings (thinner and harder). The cushion forms an additional layer under the foot in excess of 3 mm with a viscoelastic material having a thickness of 2.2 mm. This material has a hardness evaluated with a penetration index between 81 and 95 (measured according to standard NF T77-104, April 1986). The cushion happens to perfectly assume its function of compensating the plantar padding wear without affecting the posture of the user during ordinary walking. The cushion is however not adapted to sports activities. Indeed, maintaining the cushion in place on the foot is difficult in the context of an intense sports activity. Moreover, its excessive thickness tends to alter the posture of the user and the comfort of the foot in a sports shoe. It should be reminded that balance in the upright posture results from the continuous integration of data provided by three receptor systems, namely vision system, the proprioceptive system, and the vestibular system.

The vision system (position relative to the environment) and the vestibular system (detection of rotary and linear accelerations in space by the ear) would not be affected by the presence of a cushion under the foot. The situation is different for the proprioceptive system, because the perception of the ground by the cutaneous and deep mechanoreceptors is attenuated by the interposition of the cushion. However, the signals produced by these receptors result in muscular reactions that tend to cancel a conscious or unconscious sensation of imbalance. These muscular reactions may be the cause of temporary pathologies such as cramps, or longer ones like tendinitis throughout the kinematics of the body.

BRIEF SUMMARY

It may therefore be desirable to provide a cushion ensuring a load distributing function without causing a postural instability of the user, associated with retaining means capable of holding the cushion in place on the foot, also during a sports activity putting the feet under intense stress. It may also be desirable for the cushion and its retaining means to not be too bulky, so that they remain compatible with wearing shoes without discomfort. It may also be desirable for the cushion to not cause injury, especially of the toes, nor skin reactions. It may also be desirable for the cushion and its retaining means to be usable during several months and be readily manufactured.

Embodiments relate to a device for protecting the plantar padding of a foot, comprising: a cushion including a viscoelastic material, configured to be held against the skin of the plantar region, and covering the metatarsal heads and the metatarsophalangeal joints of the foot, and an elastic band attached to the cushion along two opposing transverse edges, and by a tab configured to pass between the big toe and the adjacent toe of the foot, the band having a width configured to entirely cover internal and external side bulges formed by the metatarsophalangeal joints of the small and big toes, wherein a portion of the band configured for contacting the top of the foot includes tacky elements on both sides thereof, thereby preventing the protective device from sliding on the skin when it is placed on the foot and inside a sock surrounding the foot.

According to an embodiment, the tacky elements are in the form of studs, or have a grid or honeycomb structure, and are made of polymer gel.

According to an embodiment, the tacky elements of one side of the band have a grid or honeycomb structure.

According to an embodiment, the tacky elements protrude from the surface of the fabric forming the band by 0.4 to 0.6 mm.

According to an embodiment, the cushion includes a pocket holding a pad made of viscoelastic material.

According to an embodiment, the pad is made of polymer gel having a hardness corresponding to a penetration index between 30 and 80 measured with a penetrometer, and has a thickness between 1 and 1.8 mm.

According to an embodiment, the pad is made of polymer gel having a hardness corresponding to a penetration index between 70 and 100 measured with a penetrometer, and has a thickness between 0.3 and 1 mm.

According to an embodiment, the cushion comprises an external fabric piece having a thickness between 0.5 and 1 mm, and an internal fabric piece configured to contact the skin of the foot, having a thickness between 0.2 and 0.6 mm.

According to an embodiment, the external fabric piece, the band and the tab are integral with a same piece of elastic fabric.

According to an embodiment, the band has, along the sides of the foot, a width between 35 and 45 mm.

According to an embodiment, the band has a thickness between 0.5 and 1 mm.

According to an embodiment, the cushion has a shape included within a rectangle having a length of at least 83 to 105 mm, and a width of at least 56 to 68 mm.

According to an embodiment, the band is attached to the cushion for maintaining the cushion on the foot such that a proximal edge of the cushion forms an angle between 70 and 80° with a longitudinal axis of the foot.

Other advantages and features will become more clearly apparent from the following description of particular embodiments of the invention provided for exemplary purposes only and represented in the appended drawings.

DETAILED DESCRIPTION

Figure 1A:
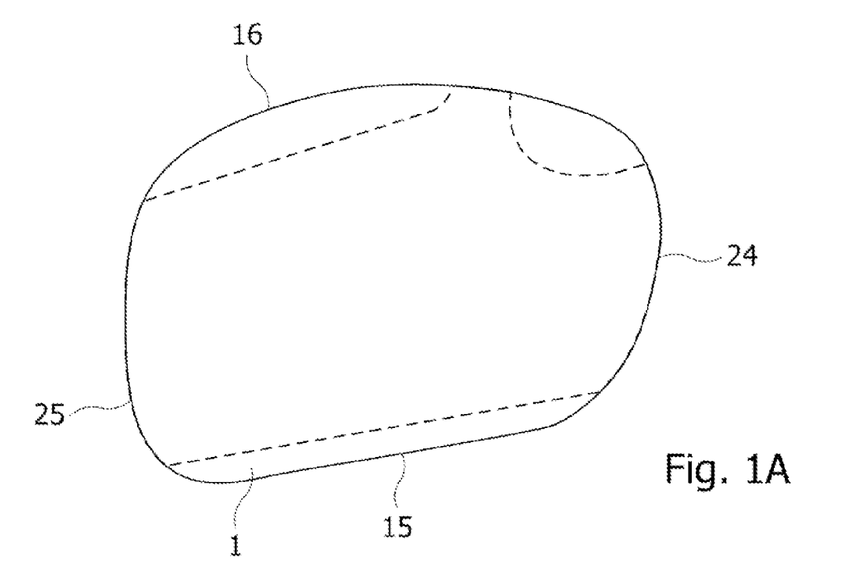
FIGS. 1A and 1B are respectively schematic bottom and top views of a foot protection device, according to one embodiment, FIG. 2 schematically shows the protection device in cross-section along the line A-A' indicated in FIG. 1B, FIG. 3 schematically shows the shape of a cushion of the protection device.
Figure 1B:
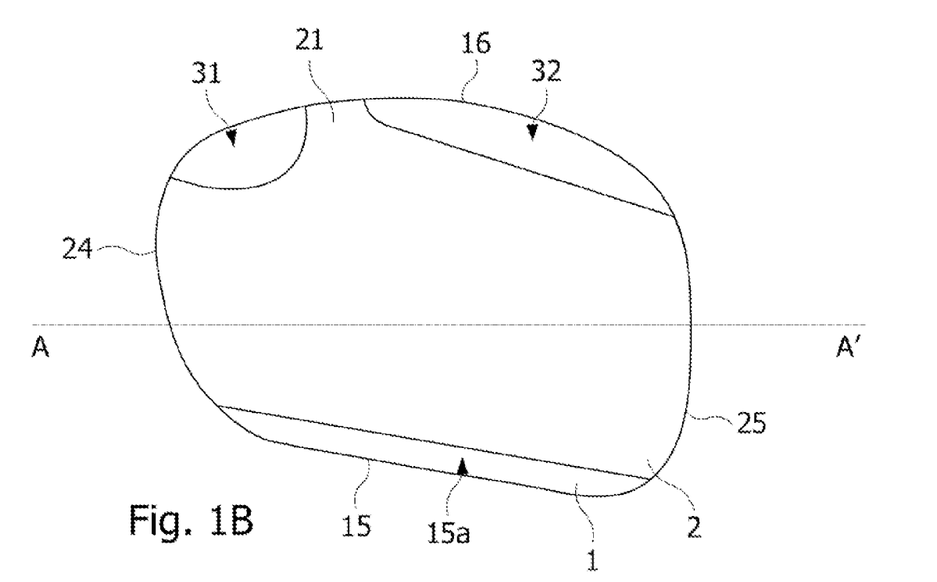
Figure 2:
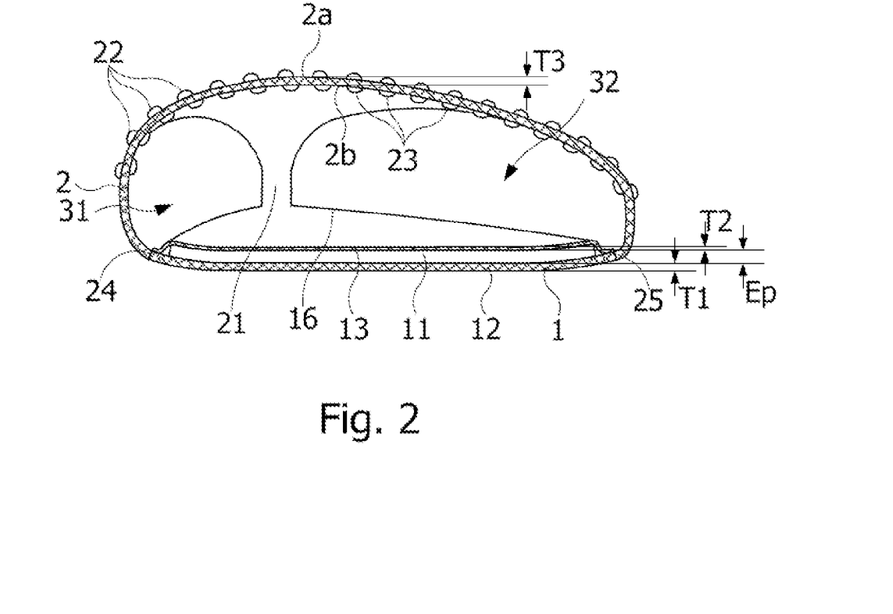

FIGS. 1A, 1B and 2 show a device for protecting the foot, according to one embodiment. The device comprises a cushion 1 and an elastic band 2 attached to the cushion 1 along two opposing transverse edges 24, 25 of the cushion. The cushion 1 together with the band 2 thus form a sleeve with a proximal opening 15a and two distal openings 31-32. The sleeve is adjusted so that it gently compresses the front of the foot. The band 2 is also attached to the cushion 1 through a tab 21 integral with the band 2 and attached to a distal longitudinal edge 16 of the cushion. The tab 21 thus delimits the two distal openings 31, 32, the opening 31 being configured for receiving the big toe of the foot, and the opening 32 being configured for receiving the other toes.

According to an embodiment, the band 2 is made of an elastic fabric, for instance run-resistant fabric, and has a thickness T3 comprised between 0.5 and 1 mm, for example about 0.6 mm.

The cushion 1 comprises a pad 11 made of a viscoelastic material configured to ensure a load distribution function. According to an embodiment, the pad is held in a pocket formed by an external fabric piece 12 assembled with an internal fabric piece 13. The shape and the dimensions of the pocket may be adjusted to fit the pad 11. The pad 11 may be glued by its entire surface on one of the two fabric pieces 12, 13, for instance the external fabric piece 12. The external and internal fabric pieces 12, 13 may be elastic and elastic and have respective thicknesses T1, T2 comprised between 0.5 and 0.8 mm, for example about 0.6 mm. According to an embodiment, the internal fabric piece 13 is thinner, having for instance a thickness T2 comprised between 0.2 and 0.6 mm, for example 0.2 mm.

According to an embodiment, the pad 11 is made of viscoelastic polymer gel, for example silicone gel. The pad 11 may thus be made of PDMS (polydimethylsiloxane), having a relatively high hardness, corresponding to a penetration index comprised between 30 and 80 (measured with a penetrometer—see standard NF T 77-104, April 1986). These penetration index values are provided for establishing comparisons between different viscoelastic materials, bearing in mind that the standard NF T 77-104 specifies limiting the index values to a range from 85 to 400. As a comparison, the pads used in the cushions for elderly people had a penetration index of 81 to 95, measured in the same conditions. The pad 11 may have a thickness Ep comprised between 1 and 1.8 mm, for example about 1.5 mm. In this manner, the overall thickness below the foot of the protection device may reach at least 1.7 mm. In the above example, the ratio of the viscoelastic material thickness to the overall thickness Ep+T1+T2 of the device below the foot may reach 71% (1.5/2.1). Under these conditions of thickness Ep and hardness of the pad 11 and of thickness T1+T2 of its enveloping fabric, the pad 11 is fit to ensure an efficient protection of a healthy plantar padding, without affecting the postural stability of the user, while occupying minimal space in the shoe.

Figure 3:
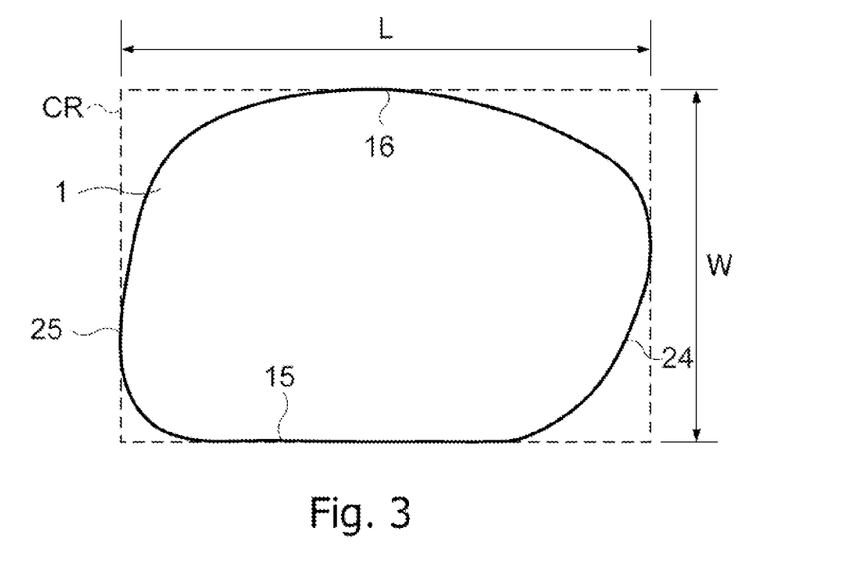

FIG. 3 shows the cushion 1. The cushion 1 fits within a rectangle CR, one long side of which coincides by more than two thirds with a proximal edge 15 of the cushion. It should be noted that the rectangle CR is the smallest rectangle in which the cushion 1 fits. According to adult foot sizes, the cushion fits in a rectangle CR having a length L comprised between 83 and 105 mm and a width W comprised between 56 and 68 mm. The rectangle CR may thus have a minimum size of 83×56 mm and a maximum size of 105×68 mm.

Figure 4:
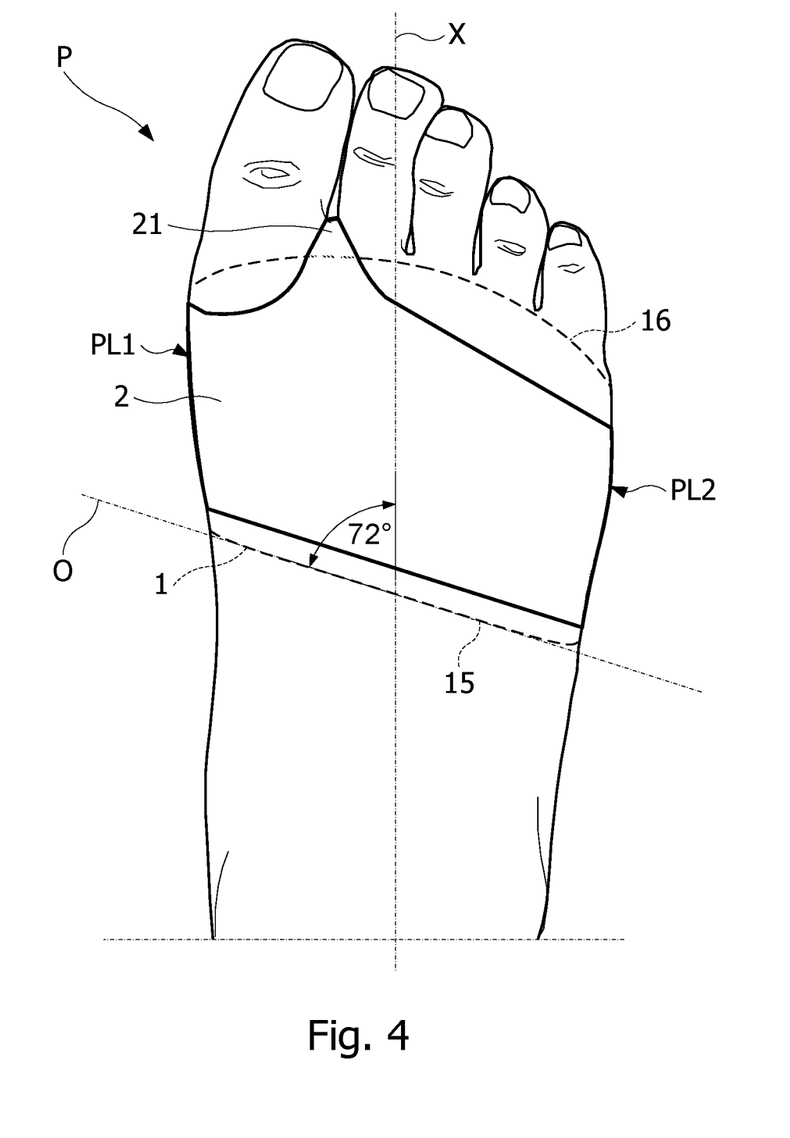
FIGS. 4 and 5 are respectively schematic top and bottom views of a foot outfitted with the protection device, FIGS. 6A and 6B schematically represent, respectively, an outer surface and an inner surface of the protection device, according to one embodiment.
Figure 5:
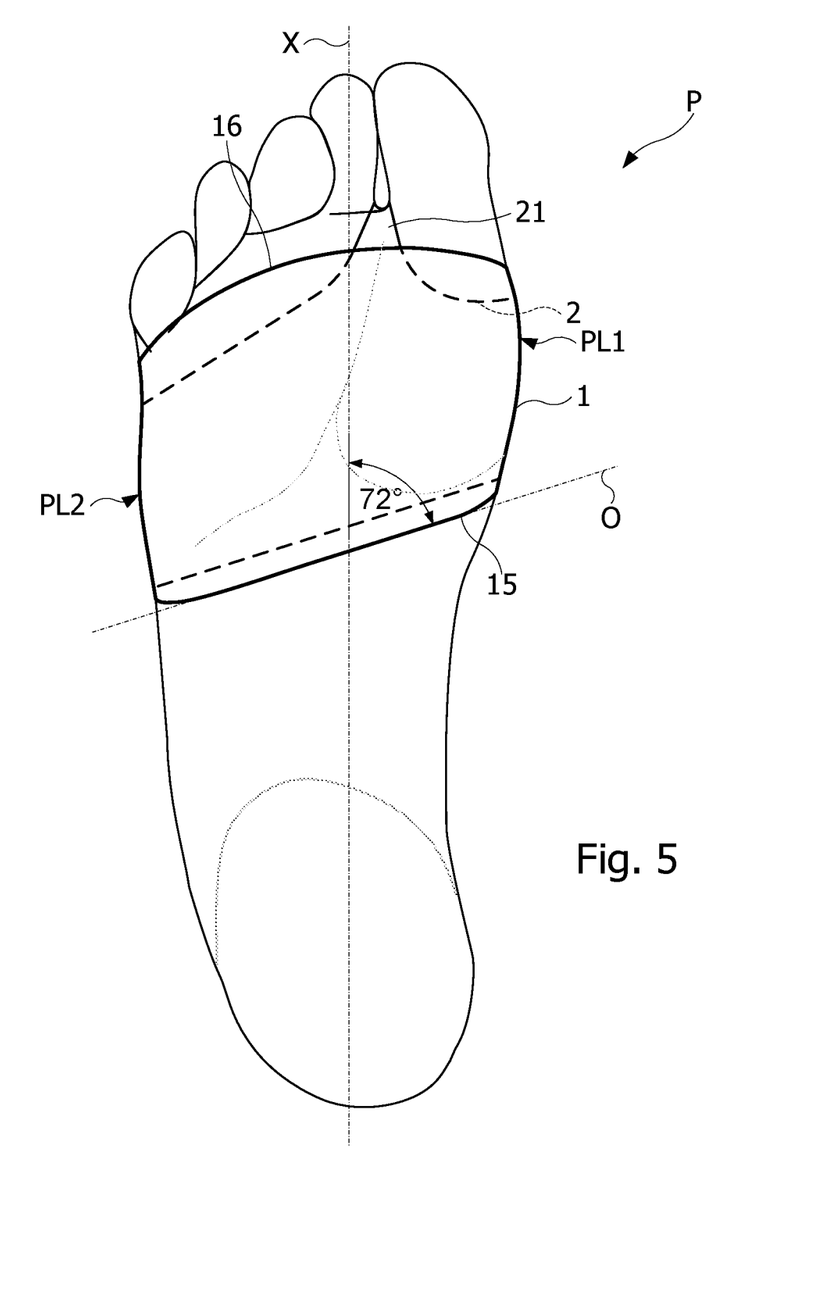

As illustrated in FIGS. 4 and 5 showing the protection device fitted on a foot, the shape and dimensions of the cushion 1 (and thus of the pad 11) are designed to cover all of the metatarsal heads and metatarsophalangeal joints of the foot, and, if necessary, part of the two lateral edges of the foot. The cushion 1 is designed to be placed on the foot so that its distal edge 16 substantially coincides with a line passing through the base of the toes in the case of an Egyptian-type foot. In this position, the proximal edge 15 of the cushion 1 extending along an axis O (corresponding to the direction of the long sides of the rectangle CR) forms an angle with the longitudinal axis X of the foot (passing through the center of the heel and the middle of the end of the second toe) between 70 and 80°, depending on the morphology of the foot. In the example of FIGS. 4 and 5, this angle is 72°.

The band 2 is configured to completely cover the internal lateral protrusion PL1 and external lateral protrusion PL2 of the foot, formed by the articulations between the metatarsal and the first phalanx of the big toe and of the small toe, respectively. It appears that this arrangement contributes to holding the cushion 1 in place on the foot, preventing in particular the sliding of the protection device along the axis of the foot. The band 2 has substantially the same width (within 15%), between 35 and 45 mm, on the lateral sides of the foot.

Figure 6A:
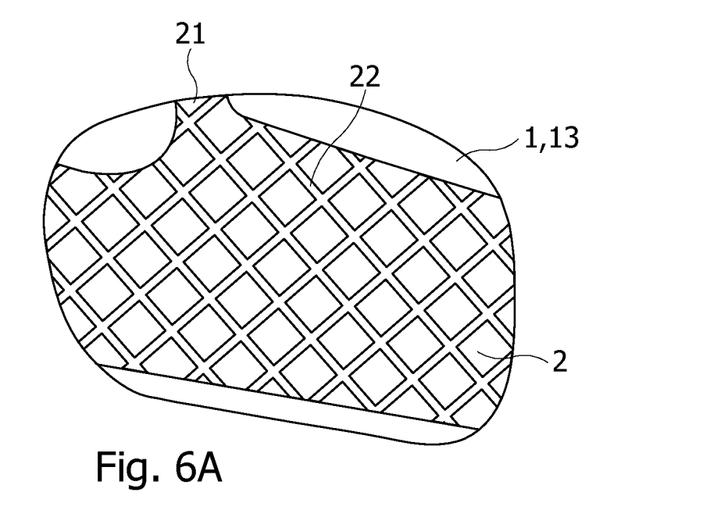
Figure 6B:
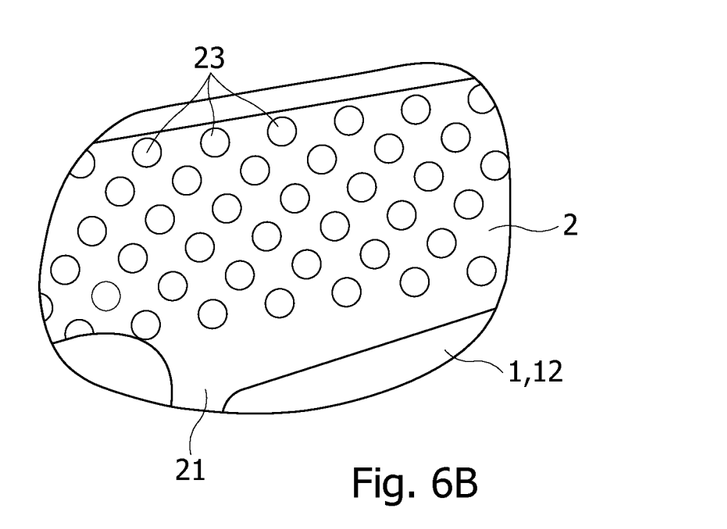

FIG. 6A shows the protection device according to one embodiment in a position showing the outer surface 2a of the band 2. FIG. 6B shows the protection device according to one embodiment in an inverted configuration in order to show the internal surface 2b of the band 2, configured to contact the skin of the foot. In embodiments illustrated in FIGS. 2, 6A and 6B, the band 2 is covered on both sides with protruding tacky elements 22, 23, designed to prevent the device from sliding on or around the foot, in particular when the device is clamped in a shoe. The clamping exerted by the elastic band 2, combined with the shape of the band and with the adhesion and the shape of the tacky elements 22 and 23, favors maintaining the protection device on the foot, including when practicing sports involving strong accelerations and sudden changes in direction. For this purpose, it is not necessary for the clamping force exerted by the band 2 around the foot to be excessive and cause discomfort to the user, even if the protection device is worn for several hours.

The tacky elements 22, 23 may be made of silicone gel, and fixed to the fabric by coating, depositing the silicone gel onto the fabric forming band 2 in sufficiently liquid form (before complete reticulation) to penetrate the fabric and obtain sufficient mechanical strength without the use of glue.

In FIG. 6A, the external tacky elements 22 formed on the outer surface 2a of the band 2 have a grid structure formed of evenly spaced parallel strips intersecting with other equally spaced parallel strips. The external tacky elements 22 can cover all or part of the tab 21 and the parts located on the lateral sides of the foot. Such a grid or honeycomb structure has the advantage of imparting a certain strength or rigidity to the fabric forming the band 2. It turns out that this feature contributes to keeping the device on the foot.

In FIG. 6B, the internal tacky elements 23 formed on the internal surface 2b of the band 2 are spherical cap-shaped studs, uniformly distributed on the internal surface 2b of the band 2, including on the parts of the band 2 that contact the lateral parts of the foot. To avoid discomfort to the user, the internal face of the tab 21 may be devoid of tacky elements.

The tacky elements 22, 23 protrude each above the surface of the fabric forming the band 2, between 0.4 and 0.6 mm. Thus, the band 2 and the tacky elements 22, 23 together have a thickness comprised between 1.5 and 2 mm, for example about 1.6 mm. This thickness added to that of the cushion 1, of the order of 4.2 mm, remains low. In this respect, it should be noted that the elements 23 partially penetrate the skin and that, in the presence of a sock, the elements 22 partly penetrate the sock, which also contributes to holding of the protection device on the foot. Under these conditions, the bulk of the protection device remains sufficiently low to be compatible with wearing socks and shoes without affecting the comfort of the user.

It should be noted that, even if the external tacky elements 22 penetrate completely into the thickness of a sock, they generate localized pressure points on the inside of the shoe, which pressure points contribute to maintaining the protection device on the foot. It should also be noted that the sock generally remains in place in the shoe without being subjected to rotational displacements around the foot. It therefore also ensures a certain retention of the band 2 by means of the external tacky elements 22.

Figure 7:
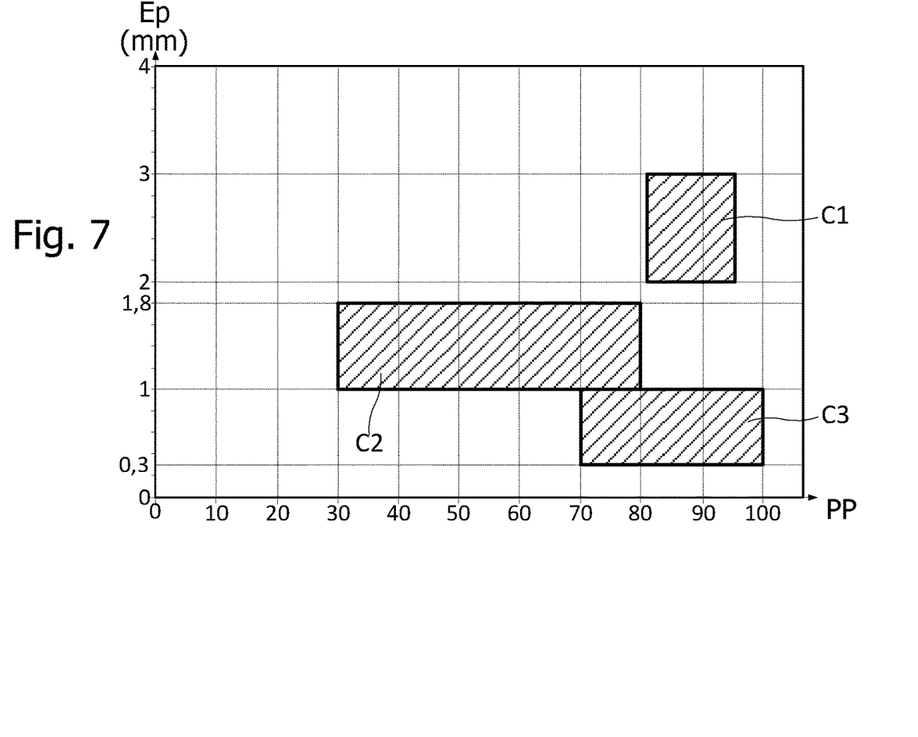
FIG. 7 shows, in the form of a graph, ranges of thickness and hardness values envisaged for the cushion, FIG. 8 schematically shows an inner or outer surface of the protection device, according to another embodiment.

FIG. 7 is a graph illustrating ranges of values envisaged for the thickness Ep and the hardness PP of the pad 11, the hardness being expressed as penetration index values measured using a penetrometer. FIG. 7 shows ranges of values C1, C2, C3. The range C1 corresponds to the values of thickness and hardness of the pad according to the prior art, used for elderly people having a worn-out plantar padding. The range C1 is defined between the hardness limits PP of 81 and 95 and the thickness limits Ep of 2 and 3 mm. The range C2 corresponds to a pad used for ensuring a load distribution function (i.e. vertical forces), with no significant effect on postural stability. The range C2 is defined between the hardness limits PP of 30 and 80 and between the thickness limits Ep of 1 and 1.8 mm.

According to one embodiment, the pad 11 may also have values of hardness and thickness belonging to the range C3. The range C3 is defined to ensure both a load distribution function and a protection function against heating of the plantar area. Such heating occurs in particular when wearing shoes having low or no damping capability, and/or when practicing sports activities involving strong accelerations directed parallel to the ground, i.e. both along the axis of the foot (when accelerating and coasting), and along a perpendicular axis, for example when suddenly changing contact points. The range C3 is defined between the PP hardness limits of 70 and 100 and between the Ep thickness limits of 0.3 and 1 mm. In the range C3, the pad 11 is softer than in the range C2 to absorb shear forces occurring under forces parallel to the ground. In the range C3, the pad 11 is also thinner than in the range C2 to limit the postural instability which may appear due to the fact that the pad is softer than in the range C2. Measurements have confirmed that the postural instability generated by a cushion containing a pad 11 belonging to the range C3 is not greater than with a pad belonging to the range C2. On the other hand, the instability is greater with a pad belonging to the range C1. The protocol used to measure the impact of the pad on postural stability includes measurement phases of a medial lateral force (parallel to the ground and perpendicular to the X axis of the foot), including a measurement phase without the cushion and measurement phases with cushions under the feet, during which testers run for a period of several minutes. The results obtained during these measurement phases allow a comparative evaluation of the magnitude of the user's compensations caused by the use of the cushions. Thus, the smaller the medial lateral force measured, the greater the compensations made by the tester to recover the same balance. It should be noted that the measurements were carried out barefoot, because wearing shoes also influences the postural stability in connection with the adequate sizing and fitting of the shoes.

At lower thicknesses, of less than 1.5 mm, the pad 11 may be formed by coating the fabric piece 12 or 13 (or 3), if necessary through multiple successive coating steps to achieve the desired thickness.

It should be noted that tacky elements, such as the tacky elements 22 or 23 may also be provided on the outer surface of the external fabric piece 12. Furthermore, the tacky elements formed on the inner surface of the band may have a grid or honeycomb structure.

Figure 8:
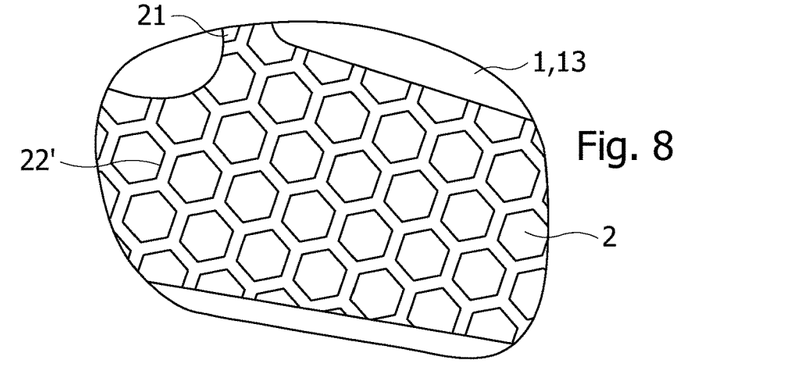

The tacky elements may have other shapes. FIG. 8 thus shows an internal or external surface of the protection device, on which tacky elements 22' are formed having a honeycomb structure. It should be noted that the grid or honeycomb structures of the tacky elements 22, 22' do not necessarily have equal length sides, since these structures may be stretched along a given direction.

Figure 9:
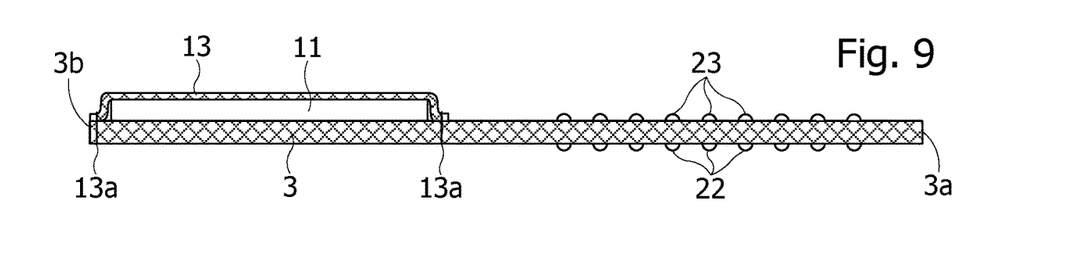
FIG. 9 is a schematic cross-sectional view of the protection device at an intermediate manufacturing step.

As illustrated in FIG. 9, showing the protection device at an intermediate manufacturing step, the device can be manufactured by making the outer fabric piece 12, the tab 21 and the band 2, described above, as a single piece of fabric 3. The pad 11 and the tacky elements 22, 23 may then be formed on, or attached to the piece of fabric 3. The inner piece of fabric 13 can then be attached to the piece of fabric 3 while covering the pad 11 and forming a pocket, for example by a seam 13a formed along the edge of the pad. The piece of fabric 3 can then be folded on itself to form a sleeve, for example by using an edge-to-edge seam between opposite edges 3a, 3b. The free end of the tab 21 can be fixed in the same manner to an opposing edge of the piece of fabric 3. In the example of FIG. 9, these seams may be achieved in part on the seam 13a.

It is not necessary for the seam 13a to extend along the entire outline of the pad 11. It is sufficient that the piece of fabric 13 does not slip, thereby allowing the pad to come into contact with the skin of the foot. Nor is it necessary for the band 2 and the external fabric piece 12 to be made of the same piece of fabric. In this case, the band 2 may be assembled with the piece 12 through three seams, namely two opposite seams and a seam for fixing the free end of the tab 21 formed in the band 2.

By virtue of these configurations, the entire device is made of materials (fabrics, silicone gel) adapted to be placed in contact with the skin for long periods of time. Furthermore, these materials have the advantage of being washable multiple times, thus allowing the protection device to be used for several months. It should also be noted that the protection device does not have large surfaces of waterproof material. Indeed, the pad 11 is not in direct contact with the skin, since the piece of fabric 13 is placed between the pad and the skin, and the tacky elements 22, 23 have small surface areas. As a result, the protection device does not impede the evacuation of perspiration, which could in particular reduce the adhesion of the device to the skin.

It will be apparent to those skilled in the art that the present invention is susceptible of various alternative embodiments. In particular, the invention is not limited to the use of silicone gel as a viscoelastic material for the pad 11 and the tacky elements 22, 23. These elements may thus be made of other materials such as neoprene, urethane polymers, and the like.

The invention claimed is:

1. A sleeve for protecting a plantar padding of a foot, the sleeve comprising:
a cushion including a pad formed of a polymer gel;
an elastic band made of an elastic fabric and attached to the cushion along two opposing transverse edges of the cushion to form the sleeve;
a plurality of tacky elements formed on an internal face of the elastic band and on an external face of the elastic band;
a first distal opening and a second distal opening, the elastic band including a tab extending from a distal longitudinal edge of the elastic band and connected to a distal longitudinal edge of the cushion, the tab separating the first distal opening from the second distal opening; and
a proximal opening, wherein:
the sleeve is configured to be worn in a fitted position where the sleeve is held against a skin of the foot around all metatarsal heads and all metatarsophalangeal joints of the foot, while (i) an upper side and a lower side of toes, (ii) an arch, and (iii) a heel of the foot are exposed outside of the sleeve, and
when the sleeve is worn in the fitted position on the foot:
the elastic band is configured to entirely cover internal and external side bulges formed by metatarsophalangeal joints of a small toe of the toes and a big toe of the toes of the foot;
the cushion covers a plantar region of the foot, and the elastic band covers an upper region of the foot, the plantar region extending under all of the metatarsal heads and the metatarsophalangeal joints of the foot;
the plurality of tacky elements has an adherence with the foot so as to prevent the sleeve from sliding along the skin and to prevent the sleeve from sliding inside a sock when a sock is worn on the sleeve; and
the first distal opening is configured to receive the big toe of the toes of the foot, and the second distal opening is configured to receive the toes other than the big toe of the foot.

2. The sleeve of claim 1, wherein the plurality of tacky elements are made of polymer gel, and the tacky elements (i) each have a stud form, (ii) have a grid structure, or (iii) have a honeycomb structure.

3. The sleeve of claim 1, wherein the plurality of tacky elements on one of the internal face or the external face of the elastic band have either a grid structure or a honeycomb structure.

4. The sleeve of claim 1, wherein the plurality of tacky elements protrude from the external face of the elastic band by 0.4 to 0.6 mm.

5. The sleeve of claim 1, wherein the cushion includes a pocket holding the pad.

6. The sleeve of claim 5, wherein the pad has a hardness corresponding to a penetration index between 30 and 80, the pad having a thickness between 1 and 1.8 mm.

7. The sleeve of claim 5, wherein the pad has a hardness corresponding to a penetration index between 70 and 100, the pad having a thickness between 0.3 and 1 mm.

8. The sleeve of claim 5, wherein the cushion includes:
an external fabric piece having a thickness between 0.5 and 1 mm, and an internal fabric piece having a thickness between 0.2 and 0.6 mm and configured to contact the skin of the foot.

9. The sleeve of claim 8, wherein the external fabric piece, the elastic band, and the tab are all integrally formed of a single piece of elastic fabric.

10. The sleeve of claim 1, wherein the elastic band has a width between 35 and 45 mm along the two opposing transverse edges of the cushion.

11. The sleeve of claim 1, wherein the elastic band has a thickness between 0.5 and 1 mm.

12. The sleeve of claim 1, wherein the cushion has a shape configured to fit within a rectangle having a length of at least 83 to 105 mm, and a width of at least 56 to 68 mm.

13. The sleeve of claim 1, wherein the elastic band is configured to maintain the cushion on the foot such that a proximal edge of the cushion forms an angle between 70° and 80° with a longitudinal axis of the foot.

* * * * *